(12) United States Patent
Dehler et al.

(10) Patent No.: US 7,766,548 B2
(45) Date of Patent: Aug. 3, 2010

(54) TRAVEL STAND FOR A MOBILE X-RAY DIAGNOSTIC MACHINE

(75) Inventors: Juergen Dehler, Forchheim (DE);
Rainer Burgkart, München (DE)

(73) Assignee: Ziehm Imaging, GmbH, Nürnberg (DE)

( * ) Notice: Subject to any disclaimer, the term of this patent is extended or adjusted under 35 U.S.C. 154(b) by 90 days.

(21) Appl. No.: 11/594,696

(22) Filed: Nov. 6, 2006

(65) Prior Publication Data
US 2008/0192895 A1    Aug. 14, 2008

(30) Foreign Application Priority Data
Nov. 5, 2005    (DE)    ........................ 10 2005 052 786

(51) Int. Cl.
*H05G 1/02*    (2006.01)
(52) U.S. Cl. ....................... 378/198; 378/197
(58) Field of Classification Search ................ 378/162, 378/166, 196, 197, 198, 205, 206, 207
See application file for complete search history.

(56) References Cited

U.S. PATENT DOCUMENTS

| 5,706,324 | A | | 1/1998 | Wiesent et al. | |
|---|---|---|---|---|---|
| 6,079,876 | A | * | 6/2000 | Schuetz | 378/205 |
| 6,092,928 | A | * | 7/2000 | Mattson et al. | 378/205 |
| 6,120,180 | A | * | 9/2000 | Graumann | 378/206 |
| 6,139,183 | A | * | 10/2000 | Graumann | 378/206 |
| 6,196,715 | B1 | | 3/2001 | Nambu et al. | |
| 6,206,566 | B1 | | 3/2001 | Schuetz | |
| 6,272,368 | B1 | * | 8/2001 | Alexandrescu | 600/407 |
| 6,359,959 | B1 | | 3/2002 | Butler et al. | |
| 6,359,960 | B1 | | 3/2002 | Wahl et al. | |
| 6,374,937 | B1 | | 4/2002 | Galando et al. | |
| 6,568,850 | B2 | * | 5/2003 | Vallin et al. | 378/205 |
| 6,851,855 | B2 | | 2/2005 | Mitschke et al. | |
| 6,890,099 | B2 | * | 5/2005 | Tanaka et al. | 378/205 |
| 6,928,141 | B2 | * | 8/2005 | Carver et al. | 378/57 |
| 7,065,393 | B2 | * | 6/2006 | Sati et al. | 600/407 |
| 2002/0099284 | A1 | * | 7/2002 | Herrmann | 600/407 |
| 2004/0258210 | A1 | * | 12/2004 | Ritter | 378/198 |

FOREIGN PATENT DOCUMENTS

DE    44 23 359    1/1996

OTHER PUBLICATIONS

Hein et al., Distortion Correction Table Compression for Volume X-ray CT Applications, In Medical Imaging 2000: Physics of Medical Imaging, Proceedings of SPIE, vol. 3977, 2000.

* cited by examiner

*Primary Examiner*—Allen C. Ho
(74) *Attorney, Agent, or Firm*—Knobbe Martens Olson & Bear, LLP

(57) ABSTRACT

A travel stand for a mobile X-ray diagnostic machine with a laser detection system containing measurement devices to determine the position of the travel stand in a spatially fixed system of coordinates is provided. The measuring devices can operate by non-contact measurement techniques and that the position of the travel stand can be determined by techniques such as triangulation. An X-ray diagnostic machine with such a position detection system offers advantages in the 3D reconstruction from 2D X-ray projection images and in navigationally guided operations under X-ray monitoring.

6 Claims, 1 Drawing Sheet

TRAVEL STAND FOR A MOBILE X-RAY DIAGNOSTIC MACHINE

CROSS-REFERENCE TO RELATED APPLICATIONS

This Application claims the benefit of the German Application DE 102 00 505 2786.8 filed Nov. 5, 2005, which is hereby incorporated by reference in its entirety.

BACKGROUND OF THE INVENTION

1. Field of the Invention

This invention generally relates to mobile X-ray diagnostic systems, and in particular, relates to devices and methods for accurately determining the position and orientation of the system.

2. Description of the Related Art

Travel stands and support carriages for mobile X-ray diagnostic machines are known in the art. U.S. Pat. No. 6,374,937 discloses a mobile C-arm X-ray machine having a motorized carriage, which enables the machine to be remotely maneuvered to travel in a path essentially perpendicular to the plane of the C-arm in order to take a series of X-ray images about the body of the patient. A measurement system can be used to detect the path traveled by the motorized carriage. The Applicant's German Patent No. 4423359B4 discloses a mobile surgical X-ray diagnostic unit having a travel stand equipped with motor-operated rollers. The machine is outfitted with incremental transmitters, enabling a motorized movement of the C-arm along the floor. A position detector is used to detect the relative position of the travel stand along a straight path.

Users of present-day X-ray diagnostic machines often desire to use mobile X-ray diagnostic machines along with instrument navigation systems to support computer-aided surgery operations (CAS) or catheter diagnostics and therapy functions. In these types of systems, a three-dimensional (3D) volumetric model can be reconstructed from a number of two-dimensional (2D) X-ray projection images. An instrument, such as a catheter for example, can be navigated through certain parts of the patient's body while using the 3D volumetric model for guidance. The quality of the 3D reconstructed model often depends on precise knowledge of the projection geometry in each 2D projection image. Due to the lighter design of most mobile X-ray diagnostic machines as compared to stationary models, the actual X-ray projection geometries often deviate from the values theoretically calculated from kinematics. In order to remedy this drawback, these deviations are typically determined in a calibration run and placed in correction tables. This built-in calibration adjustment provides substantial improvement in the quality of the 3D reconstruction when the texture of the floor underneath the travel stand during calibration, which usually takes place at the factory, are virtually identical to the texture of the floor in an operating room where the medical procedure takes place. But this is often not the case and thus additional deviations arise, which usually cannot be determined in a calibration run. The deviations may be produced, for example, by the pressing of the rollers of the travel stand into an elastic floor covering, by a temporary or permanent flattening of the running surfaces of the rollers, or also by the spatially different elasticity of the floor, which occurs, for example, with hollow floors or floors with partial supports.

Partial differences in the elasticity and/or in the inclination of the floor also pose a problem and affect the accuracy of the system when, for example, it is necessary to track the path of a catheter tip in a subject and the path being observed has a greater length than the largest dimension of the X-ray receiver. In this case, an X-ray projection of the path must be put together from several smaller projection images, and the X-ray diagnostic machine usually has to move across the floor to obtain these different images. The same is true for the case when one has to create a volume model of a rather large and lengthy region of investigation from 2D projection images.

A mobile X-ray diagnostic machine can be used in conjunction with a navigational system for instrument navigation in a reconstructed 3D X-ray volume if the position of the reconstructed X-ray volume is known in relation to the system of coordinates of the navigational system. For this, the means of measurement provided in prior art systems are generally inadequate, since deviations of the floor from the horizontal and/or local fluctuations in the elasticity often cause false readings of position determination of the reconstructed X-ray volume.

The present invention is intended to ameliorate at least one of the drawbacks described above. To this end, certain embodiments of the present invention provide a mobile X-ray diagnostic machine which enables a determination of the orientation of the travel stand or cart in a spatially fixed system of coordinates even when the floor is uneven and/or has local differences in its elasticity.

SUMMARY OF THE INVENTION

In one embodiment, the present invention provides an X-ray diagnostic system arranged on a cart or carriage support which carries a position detection system, outfitted with a reference body, which determines the position of the reference body in space and relays it to a control unit of the X-ray diagnostic machine to determine the 2D projection geometry.

In another embodiment, the present invention provides a mobile X-ray diagnostic machine for generating 2D X-ray projection images for a volume reconstruction with an X-ray source/X-ray receiver unit. The X-ray units are arranged on a C-arm capable of multiple motorized movements. The machine further includes a travel stand which can travel over a floor. The machine further comprises a laser detection system arranged on a reference body of the travel stand. The laser detection system is adapted to determine the position of the reference body in a spatially fixed system of coordinates and relays the position of the reference body to a control and image processing computer to calculate the particular X-ray projection geometry each time.

In yet another embodiment, the present invention provides a method of determining position and orientation of an X-ray diagnostic system for the purposes of creating an accurate 3D reconstruction of 2D X-ray images. The method comprises the step of determining the position of a reference body on the system in a spatially fixed system of coordinates, relaying the position of the reference body to a control and image processing system, and calculating the X-ray projection geometry based on the position of the reference body.

DETAILED DESCRIPTION OF THE PREFERRED EMBODIMENT

Figure 1:
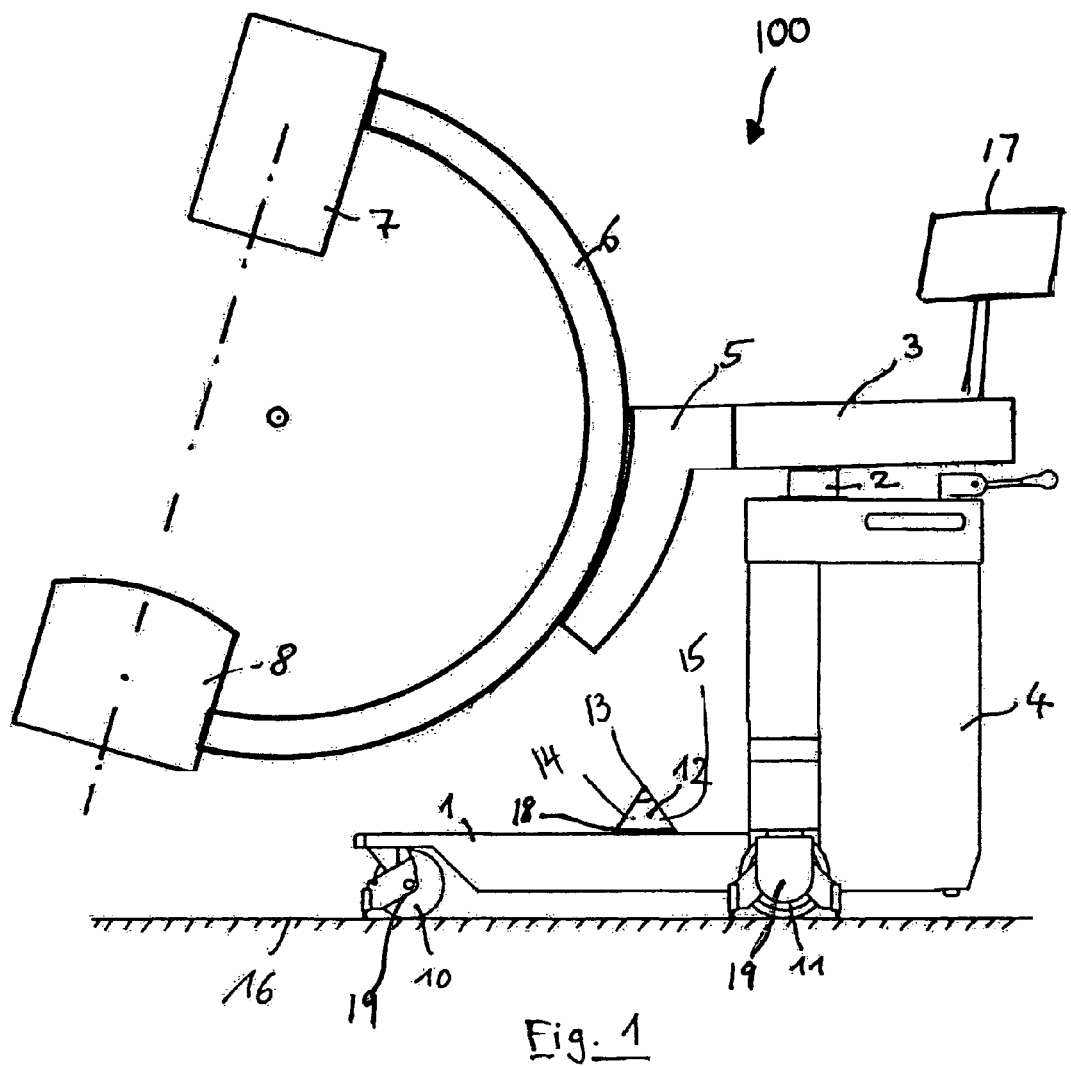
FIG. 1 schematically illustrates a mobile X-ray diagnostic system of one embodiment having a travel stand incorporating a position detection system.

FIG. 1 schematically illustrates an X-ray diagnostics imaging system 100 of one preferred embodiment of the present invention.

As shown in FIG. 1, the system 100 generally comprises an X-ray source 8, an X-ray receiver 7, a C-arm 6, a travel stand 1, a control and image processing computer 17, and an instrument cabinet 4. The C-arm 6 is shaped roughly like a circular arc. The X-ray source 8 is disposed on one end of the C-arm 6 and the X-ray receiver 7 is disposed at the other end of the C-arm 6. The X-ray source 8 and receiver 7 are mounted facing each other on opposing ends of the C-arm 6 in a manner known in the art. As FIG. 1 further shows, the C-arm 6 is mounted to a support 5, which is able to move along its circumference and outfitted with a position sensor for the movement and preferably with an electric motor drive unit. The support 5 is arranged on a horizontal guide 3, likewise preferably driven by an electric motor and provided with a position sensor. The support 5 is mounted on a vertical column 2 which can adjust its height by electric motor. A guideway of the column 2 is preferably fixedly coupled to the travel stand 1, which also carries the instrument cabinet 4.

The travel stand 1 has steerable rollers 10, 11, preferably driven by motor, which can travel over a floor 16. On the travel stand 1 there is arranged a position detection system 12, such that the orientation of a reference body 13 connected to the position detection system 12 can be determined in space. In one embodiment, the position detection system 12 can have a noncontact type arrangement of distance sensors, through which markings that are fixed in space are identified and their distance from the position detection system 12 is determined. The orientation of the reference body 13 can be determined by using a known triangulation technique or other techniques known in the art. In one implementation, the position detection system 12 has an inclination sensor 18. In another implementation, incremental sensors 19 are coupled to the wheels 10, 11.

In one embodiment, the position detection system 12 comprises a laser detection system 14, which is capable of determining the inclination of a reference surface on the travel stand and a path measuring system 15 to determine the position of the travel stand 1 in relation to the floor 16. Such a path measuring system 15 can be an arrangement of measuring balls rolling along the floor or noncontact-working path measuring systems, such as laser or LED measurement systems. Moreover, in one embodiment, magnetic or electromagnetic sensors are used for the path measuring system, interacting with guide wires or structures in the floor which can be sensed in this way. The path measuring system is adapted to determine the coordinates of the travel stand 1 relative to a system of coordinates fixed to the floor at the start of the translatory movement. For this, one specifies the placing of a mark on the floor, which can be identified by the path measuring system, thus fixing the origin and the axes of the system of coordinates fixed in space or to the floor, and the translation movements of the travel stand 1 are related to it.

Although the foregoing description of the preferred embodiments of the present invention has shown, described and pointed out the fundamental novel features of the invention, it will be understood that various omissions, substitutions, and changes in the form of the detail of the invention as illustrated as well as the uses thereof, may be made by those skilled in the art, without departing from the spirit of the invention. Particularly, it will be appreciated that the preferred embodiments of the invention may manifest itself in other shapes and configurations as appropriate for the end use of the article made thereby.

What is claimed is:

1. A mobile X-ray diagnostic machine for generating 2D X-ray projection images for a volume reconstruction, comprising:
    a C-arm capable of multiple motorized movements;
    an X-ray source, an X-ray receiver unit, wherein the X-ray source and the X-ray receiver unit are arranged on the C-arm;
    a control and image processing computer; and
    a travel stand which can travel over a floor, wherein the travel stand comprises a reference body, a position detection system connected to the reference body, said position detection system comprises a laser detection system, a path measuring system, and an inclination sensor, said laser detection system is arranged on the reference body and is adapted to determine a position of the reference body in a spatially fixed system of coordinates and relays the position of the reference body to the control and image processing computer to calculate a particular X-ray projection geometry, said path measuring system is capable of determining a position of the travel stand in relation to the floor, said inclination sensor is adapted to determine an inclination of a reference surface of the travel stand.

2. The mobile X-ray diagnostic machine according to claim 1, wherein the path measuring system comprises laser distance measuring sensors, which are adapted to determine the distances of the position detection system from spatially fixed markings.

3. The mobile X-ray diagnostic machine according to claim 1, wherein the travel stand has at least three measuring wheels and a plurality of incremental sensors coupled to the wheels, wherein the wheels are adapted to contact the floor, wherein the rotation of the wheels is detected by the incremental sensors.

4. The mobile X-ray diagnostic machine according to claim 1, wherein the inclination sensor is adapted to determine the inclination of a reference surface of the travel stand relative to the direction of the acceleration due to gravity and wherein the path measuring system comprises noncontact type optical path measuring sensors adapted to determine the relative translation of the travel stand relative to the floor.

5. The mobile X-ray diagnostic machine according to claim 4, wherein the path measuring sensors are adapted to detect a periodic electrical structure in the floor.

6. The mobile X-ray diagnostic machine according to claim 4, wherein the path measuring sensors are adapted to detect a periodic magnetic structure in the floor.

* * * * *